United States Patent
Bandyopadhyay et al.

(10) Patent No.: US 6,531,166 B2
(45) Date of Patent: Mar. 11, 2003

(54) USE OF BETEL LEAF EXTRACT TO INDUCE IFN-GAMMA PRODUCTION FROM HUMAN PERIPHERAL BLOOD T CELLS AND AS A TH₁ TYPE IMMUNOMODULATOR

(75) Inventors: Santu Bandyopadhyay, Calcutta (IN); Bikash Pal, Calcutta (IN); Samir Bhattacharya, Calcutta (IN); Mitali Ray, Calcutta (IN); Keshab Chandra Roy, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/746,017

(22) Filed: Dec. 26, 2000

(65) Prior Publication Data

US 2002/0146470 A1 Oct. 10, 2002

(51) Int. Cl.⁷ ................................................. A61K 35/78
(52) U.S. Cl. ........................ 424/774; 424/725; 424/727; 514/885
(58) Field of Search ................................ 424/725, 727, 424/774; 514/885

(56) References Cited

U.S. PATENT DOCUMENTS 5,389,371 A * 2/1995 Shiao
6,228,347 B1 * 5/2001 Hersh

FOREIGN PATENT DOCUMENTS

| JP | 06078714 | * 3/1994 |
| JP | 09278666 | * 10/1997 |
| JP | 10077495 | * 3/1998 |
| JP | 11130685 | * 5/1999 |
| JP | 200290165 | * 10/2000 |

OTHER PUBLICATIONS

Trivedi et al. 1994. Neoplasma. vol. 41, No. 3, pp. 177–181.*

The American Pharmceutical Assoc. Practical Guide to Natural Medicines. 1999. Publisher: William Morrow and Co., Inc. New York. pp. 74–75.*

PDR for Herbal Medicines. 1998. Publisher: Medical Economics Co., Montvale, NJ. pp. 1041–1042.*

* cited by examiner

Primary Examiner—Christopher R. Tate
(74) Attorney, Agent, or Firm—Sughrue Mion, PLLC

(57) ABSTRACT

This invention relates to use of betel leaf extract to induce IFNγ from human peripheral blood mononuclear cells and as a Th₁ type immuno modulator, wherein the said method comprises the steps of, preparing water extract of betel leaf, preparation of human peripheral blood mononuclear cells, incubation of hPBMC with betel leaf extract for a period of 18–48 hours, extraction of RNA for cytokine specific RT-PCR or for flow cytometry for the detection of intracellular cytokine protein, subjecting RNA for RT-PCR to obtain PCR products using IFNγ specific known primers, and enhancement of IFNγ as reflected by IFNγ specific band.

12 Claims, 2 Drawing Sheets

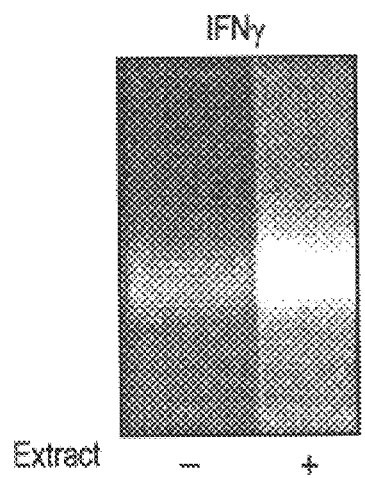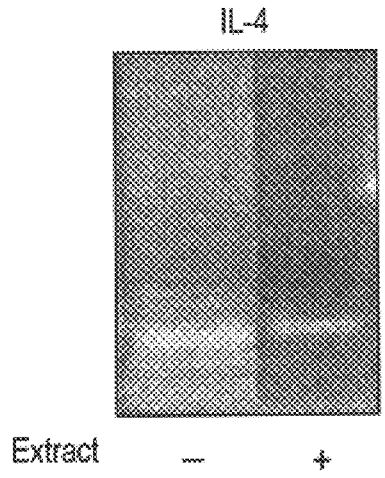

Figure 2A:
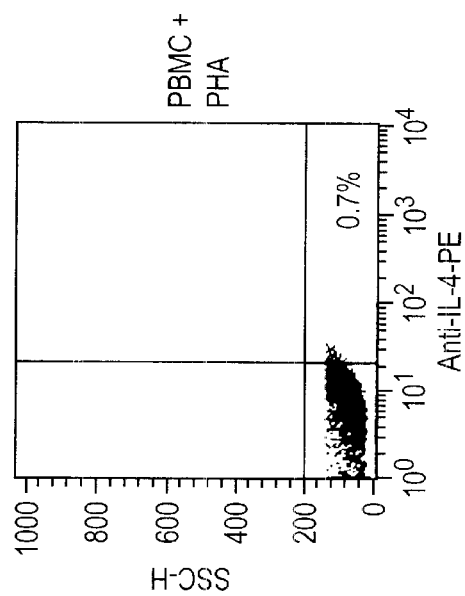

USE OF BETEL LEAF EXTRACT TO INDUCE IFN-GAMMA PRODUCTION FROM HUMAN PERIPHERAL BLOOD T CELLS AND AS A TH$_1$ TYPE IMMUNOMODULATOR

FIELD OF THE INVENTION

This invention relates to use of betel leaf extract to induce IFN-gamma production from human peripheral blood T cells.

BACKGROUND AND PRIOR ART REFERENCES

Stinging nettle leaf extracts are registered in Germany for adjuvant therapy of rheumatic diseases. In a whole blood culture system, the nettle extract IDS 23 (Rheuma-Hek) inhibited lipopolysaccharide stimulated monocyte cytokine expression, indicating an immunomodulating effect. (Antirheumatic Effect of IDS 23, a Stinging Nettle Leaf Extract, on in vitro expression of T helper cytokines). The applicants investigated the immunomodulating effects of betel leaf extracts on phytohemagglutinin (PHA) stimulated peripheral blood mononuclear cells (PBMC) in vitro. Betel leaves has a strong pungent aromatic flavor and widely used as a masticatory. Generally, mature or over mature leaves, which has ceased growing but not yet become brittle are used for chewing. The basic preparation for chewing purposes consists of betel leaf smeared with hydrated lime and catechu to which scrapings of arecanut are added; flavorings such as coconut shavings, clove, cardamon, fennel, powdered liquorice, nutmeg and also tobacco are used according to one's taste. In some places prepared pan is covered with silver or gold leaf. As a masticatory, it is credited with many properties: it is aromatic, digestive, stimulant and carminative. Medicinally it is useful in catarrhal and pulmonary affections; it is also used for poultices. The effects of chewing of betel with arecanut and other adjuncts are the excitation of the salivary glands and the irritation of the mucous membrane of the mouth. The red coloration produced is due to a pigment in the arecanut, which manifests itself under the action of alkali in lime and catechu. A mild degree of stimulation is produced, resulting in a sensation of warmth and well being, besides imparting a pleasant odor. The most important factor determining the aromatic value of the leaf is the amount and particularly the nature of the essential oil present. Betel leaves from different regions vary in smell and taste. The most pungent is the Sanchi type, while the most mild and sweet ones are from Madras. The betel leaves contain essential oils, the content of oil varies from 0.7 to 2.6 per cent depending upon the varieties of leaves. The oil consists of phenols and terpens. The higher the proportion of phenol oil, the better the quality. An isomer of eugenol named chavibetol (betel phenol; 4-allyl-2-hydroxy-1-methoxy benzene) is considered to be the characteristic constituent of betel oil. It is however, absent in Indian samples. Betel oil of Indian types contain as a predominant phenolic constituent. Oil of betel has been used in the treatment of various respiratory catarrhs, under as a local application either by gargle or by inhalation in diphtheria. It has carminative properties. It exhibits in different action on the central nervous system of mammals; lethal doses produce deep narcosis leading to death within a few hours. The essential oil and extracts of the leaves possess activity against several Gram-positive and Gram-negative bacteria such as *Micrococcus pyogenes* var. *albus* and var. *aureus, Bacillus subtilis* and *B. megaterium, Diplococcus pneumoniae, Streptococcus pyogenes, Escherichia coli, Salmonella typhosa, Vibrio comma, Shigella dysenteriae, Proteus vulgaris, Pseudomonas solanacaerum, Sarcina lutea* and *Erwinia carotovora*. The oil is found to be lethal in about 5 minutes to the protozoa *Paramaecium caudatum* (Wealth of India, Vol.8 pp.84–94). It inhibits the growth of *Vibrio cholerae, Salmonella typhosum* and *Shigella flexneri* and *Escherichia coli*. Steam—distillate of the leaves showed activity against *Mycobacterium tuberculosis*.

OBJECTS OF THE INVENTION

The main object of the present invention is to provide a method for inducing IFN-γ from human peripheral blood mononuclear cells.

Another object of the present invention relates to use of betel leaf extract for inducing IFN-γ production from human peripheral blood T cells.

Another object of the invention is to provide a composition comprising betel leaf extract, which is useful as Th$_1$ type immunomodulator.

SUMMARY OF THE INVENTION

To meet the above objects, the present invention provides a method for inducing IFN-γ from human peripheral blood mononuclear cells. The invention also relates to use of betel leaf extract for inducing IFN-γ production from human peripheral blood T cells.

DETAILED DESCRIPTION OF THE INVENTION

Accordingly, the invention relates to a method for inducing IFNγ from human peripheral blood mononuclear cells wherein the said method comprising preparing water extract of betel leaf; preparation of human peripheral blood mononuclear cells; incubation of hPBMC with betel leaf extract for a period of 18–48 hours; extraction of RNA for cytokine specific RT-PCR or for flow cytometry for the detection of intracellular cytokine protein; subjecting RNA for RT-PCR to obtain PCR products using IFNγ specific known primers and enhancement of IFNγ as reflected by IFNγ specific band.

Alternatively, one more method for inducing IFNγ produced from human peripheral blood mononuclear cells wherein the said process comprising subjecting incubated cells for intracellular staining for IFNγ; analysis of stained cells in flow cytometer; and enhancement of IFNγ positive cells to at least seven fold.

A method for using betel leaf extract as Th$_1$ type immunomodulator wherein the said method comprising:
 a) administering to a subject at least 5 to 10 mg/ml/kg body wt. of betel leaf extract, and
 b) administering the extract through oral or intramuscular route once in a day for a period of at least one month, In an embodiment of the present invention provides a pharmaceutical composition useful as Th$_1$ type immunomodulator, said composition comprising an effective amount of betel leaf aqueous extract or lyophilized betel leaf extract together with or associated with an additive.

In still another embodiment of the invention, the additive is selected in such a manner that does not interfere with the activity of betel leaf extract.

Yet another embodiment of the invention, the additive is selected from nutrients such as proteins, carbohydrates, sugar, talc, magnesium stearate, cellulose, calcium carbonate, starch-gelatin paste and/or pharmaceutically acceptable carriers, excipient, diluent or solvent.

Yet another embodiment of the invention, the aqueous extract, lyophilized product or the composition is administered orally or intramuscularly.

Yet another embodiment of the invention, the oral route is in the form of capsule, syrup, concentrate, powder or granules.

Yet another embodiment of the invention, the ratio of betel leaf extract to the additive is in the range between 10-1:1-10.

Yet another embodiment of the invention, the betel leaf extract, lyophilized extract or the composition comprising the betel leaf extract is administered at a dosage level between 5 to 10 mg/kg of body weight at least once in a day for one month.

In one more embodiment of the present invention, a method of treating a subject to provide Th1 type immunomudulation, said method comprising administering a pharmaceutically effective amount of betel leaf extract, lyophilized extract or a composition comprising the extract to the subject.

Yet another embodiment of the present invention, the additive is selected in such a manner it does not interfere with the activity of lyophilized betel leaf extract.

Yet another embodiment of the invention, the additive is selected from nutrients such as proteins, carbohydrates, sugar, talc, magnesium stearate, cellulose, calcium carbonate, starch-gelatin paste and/or pharmaceutically acceptable carriers, excipient, diluent or solvent.

Yet another embodiment of the invention, the aqueous extract, lyophilized product or the composition is administered orally or intramuscularly.

Yet another embodiment of the invention, the oral route is in the form of capsule, syrup, concentrate, powder or granules.

Yet another embodiment of the invention, the ratio of betel leaf extract to the additive is in the range between 10-1:-10.

Yet another embodiment of the invention, the betel leaf extract, lyophilized extract or the composition comprising the betel leaf extract is administered at a dosage level between 5 to 10 mg/kg of body weight at least once in a day for one month.

In one more embodiment of the present invention, use of betel leaf extract in association with suitable carriers/additive as $Th_1$ type immunomodulator.

Yet another embodiment of the present invention, the additive is selected in such a manner it does not interfere with the activity of lyophilized betel leaf extract.

Yet another embodiment of the invention, the additive is selected from nutrients such as proteins, carbohydrates, sugar, talc, magnesium stearate, cellulose, calcium carbonate, starch-gelatin paste and/or pharmaceutically acceptable carriers, excipient, diluent or solvent.

Yet another embodiment of the invention, the aqueous extract, lyophilized product or the composition is administered orally or intramuscularly.

Yet another embodiment of the invention, the oral route is in the form of capsule, syrup, concentrate, powder or granules.

Yet another embodiment of the invention, the ratio of betel leaf extract to the additive is in the range between 10-1:1–10.

Yet another embodiment of the invention, the betel leaf extract, lyophilized extract or the composition comprising the betel leaf extract is administered at a dosage level between 5 to 10 mg/kg of body weight at least once in a day for one month.

One more embodiment of the present invention relates to the preparation of betel leaf extracts comprising the following steps;

1) washing of the fresh leaves of Piper betel and homogenizing in a mixture blender;

2) sonicating in an ultrasonic bath with 2 to 3 bursts each for 15 minutes and filtering the extract, if desired repeating the extraction at least once and drying; and 3) lyophilizing the extract to get a semi-solid mass In one more embodiment of the invention, the lyophilized extract is obtained by freeze drying the aqueous extract by conventional methods.

In another embodiment, the water extract is prepared from following types of betel leaf (*Piper betel*) namely Wild type, Climber type, Bangla type and Sweet type.

BRIEF DESCRIPTION OF THE ACCOMPANYING DRAWINGS

FIG. 1: represents RT-PCR to demonstrate that betel leaf extract enhances IFN-γ mRNA expression by peripheral blood mononuclear cells (PBMC) of normal individuals.

Figure 2B:
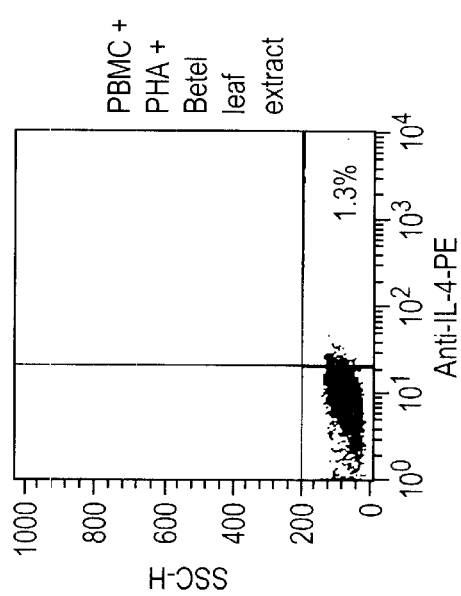
Figure 2C:
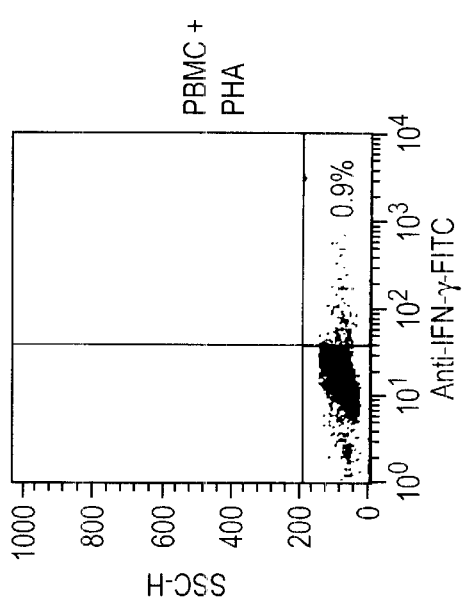
Figure 2D:
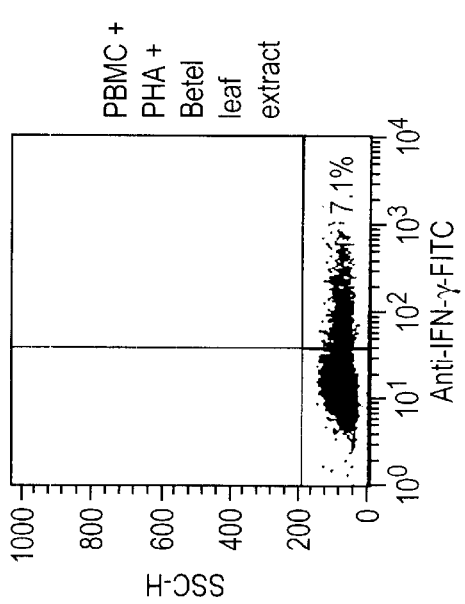

FIG. 2: represents flow cytometric determination that betel leaf extract enhances IFN-γ expression at the protein level by PBMC of normal individuals.

The following examples further illustrate the invention, but the invention is not limited thereto.

EXAMPLE 1

34.14 gm of fresh leaves of *Piper betle* thoroughly washed in sterile water was homogenized with 100 ml of glass distilled water in a mixture-blender. It was then sonicated in an ultrasonic bath with 3 burst each for 15 min. The extract was filtered through Whatman No.1 filter paper and the filtrate was collected. This process of extraction was repeated three times. The combined extract was lyophilized yielding a semi-solid mass weighing 1.17 gm. This was then tested for biological activity.

EXAMPLE 2

The fresh leaves of *Piper betle* weighing 21.68 gm homogenized with distilled water (60 ml) in a mixture-blender and then sonicated in an ultrasonic bath with 2 burst each for 15 min. It was allowed to be extracted overnight or 16 hours. Filtering through Whatman No.1 filter paper separated the material extracted in water. This type of treatment for extraction was repeated for three times. The combined extract was evaporated to dryness in a flash evaporator under reduced pressure at 45° C. The residual substance was then dried in a desiccator under high vacuum and the semi-solid mass weighing 0.59 gm was tested for biological activity.

Properties of the Materials

The biologically active material obtained by examples 1 and 2 has the following properties:

1) The dried semisolid prepared as stated above was a dark colored material soluble in water and dimethyl sulfoxide.

2) Thin layer chromatography of the active material shows five spots having $R_f$ 0.75, 0.64, 0.50, 0.40 and 0.33 in the solvent system of n-butanol, acetic acid and water in the ratio of 9:5:7 respectively.

3) The HPLC analysis of the active material using Intersil ODS-3 (4.6×250 mm) analytical column, solvent system methanol and water in the ratio of 4:1 and a flow rate of 1.0 ml/min., detection at 217 nm resolved the material into eleven peaks with the retention time of 2.69, 4.27, 5.95, 6.97, 7.49, 9.39, 11.20, 12.40, 15.53, 18.90 and 21.49 mins.

EXAMPLE 3

1. Preparation of human peripheral blood mononuclear cells (PBMC):

Heparinized whole bloods (collected from normal individuals) were subjected to Ficoll Hypaque density gradient centrifugation. Cells in the interface were washed twice with phosphate buffered saline (PBS) and then re-suspended in medium RPMI-1640 supplemented with 10% Fetal Bovine Serum.

2. Incubation of hPBMC with betel leaf extract:

PBMC ($5.0 \times 10^6$ cells) were cultured overnight (18 hours) at 37° C. in 5% $CO_2$ in a total volume of 2.0 ml RPMI+10% FBS containing 5 µg/ml of phytohemagglutinin (PHA) in 24 well plates in the presence or absence of betel leaf extracts (12.5 mg/ml final concentration). At the end of the incubation period PBMC were washed twice with PBS and used for extraction of total RNA for cytokine specific RT-PCR or for flow cytometry for the detection of intracellular cytokine at the single cell level.

3. RNA preparation and RT-PCR

Total cellular RNA from cultured PBMC was extracted by Trizol (Gibco BRL). $5 \times 10^6$ cells were cultured for 18 hours as described above and harvested and resuspended in 1 ml Trizol. 2 µg of RNA and 10 µm of each primers were used to synthesize cDNA and PCR in single tube using superscript™ One step RT-PCR system (Gibco BRL) in a total volume of 25 µl-Primer sequences of human IFNγ and human IL-4 were as follows:

IFNγ sense, 5' TCT GCA TCG TTT GGG TTC CT 3', (SEQ ID NO: 1), IFNγ antisense 5' CAG CTT TTC GAA GTC ATC TC 3' (SEQ ID NO: 2); IL-4 Sense 5' CCT CTG TTC TTC CTG CTA GC 3' (SEQ ID NO: 3); IL-4 antisense 5' CCG TTT CAG GAA TCG GAT CA 3' (SEQ ID NO: 4). Amplification and cDNA synthesis was performed as described in manufacturer's protocol. PCR products were electrophoresed in a 1.2% agarose gel in the presence of ethidium bromide and photographed under ultraviolet transmilluminator. Molecular weight markers (123 bp ladder, Gibco BRL) were included in all gels. (J. Rheumatol. 1999: 26, 2517–2522)

4. Flow cytometry

Cells were washed, permeabilized by treatment with 4% paraformaldehyde for 10 min., followed by incubation with 0.1% saponin for 10 min. Cells were then washed with washing buffer (PBS containing 1% albumin, 0.1% saponin and 0.1% sodium azide). After washing, permeabilized cells were treated with FITC or PE labeled control monoclonal antibody (mAb), anti-human IFNγ Ab labeled with FITC or anti-human IL-4 mAb labeled with PE, for 20 min. in room temperature at dark. Cells were then washed once with washing buffer and once with PBS and then resuspended in PBS containing 1% paraformaldehyde for flow cytometric analysis.

Results:

Influence of Betel leaf extract on $Th_1$ cytokine expression

It is clear that FIG. 1, that betel leaf extract enhances IFNγ mRNA expression but has no effect on IL-4 m RNA expression by peripharal blood mononuclear cells of normaL human individuals as determined by RT-PCR. In other words, the applicants' data as shown in FIG. I indicates that betel leaf extract significantly enhances synthesis of IFNγ specific mRNA and having virtually no effect on IL-4 mRNA sysnthesis.

IFNγ synthesis by PBMC was also detectable at the protein level as evident from the flow cytometric dot plot analysis as shown in FIG. II. Only 0.9% PBMC were positive for IFNγ when PBMC were incubated with PHA (FIG. IIA). On the other hand, 7.1% PBMC showed intracellular IFNγ (FIG. IIB) when PBMC were incubated with PHA plus betel leaf extract. In contrast, percentages of IL-4 producing cells were not appreciably changed when PBMC were incubated with betel leaf extract (FIG. II C & D).

Discussion

T cells are subdivided into $Th_1$ and $Th_2$ phenotypes by their cytokine patterns (Mossmann, T. R., Coffman, R L. $Th_1$ and $Th_2$ cells: different patterns of lymphokine secretions lead different functional properties. Annual Rev. Immunol. 1989, 7; 145–73), which regulate cell mediated and humoral immune responses. Inflammatory immune responses are primarily mediated by $Th_1$ cell polpulations through the production of $IL_2$ & IFN-γ, which enhance cellular immunity (Trinchieri G. Interlenkin-12 and its role in generation of $Th_1$ cells. Immunol Today 1993; 14: 335-8; Germann, T., Szeliga, J., Hess, H. et al. Administration of interlenkin-12 in combination with type-II collagen induces severe arthritis in DBA/1 mice. Proc Natl Acad Sci. USA 1995; 92: 4823–7).

Thus, our experimental results suggest that betel leaf extracts enhance $Th_1$ type response leading to enhanced cellular immunity.

What is claimed is:

1. A method of enhancing a cellular immune response mediated by $Th_1$ helper T-lymphocytes in a subject, said method comprising administering a pharmaceutically effective amount of a composition comprising a betel leaf extract to a subject in need of such enhancing, wherein the betel leaf extract is obtained by aqueous extraction of betel leaves, thereby enhancing a cellular immune response mediated by $Th_1$ helper T-lymphocytes.

2. The method as claimed in claim 1, wherein the composition comprising the betel leaf extract is associated with or in combination with a pharmaceutically acceptable additive.

3. The method as claimed in claim 1, wherein the betel leaf extract has further been lyophilized.

4. The method as claimed in claim 3, wherein the composition comprising the betel leaf extract is associated with or in combination with a pharmaceutically acceptable additive.

5. The method as claimed in claims 2 or 4, wherein the additive does not interfere with the activity of said betel leaf extract.

6. The method as claimed in claims 2 or 4, wherein the additive is a pharmaceutically acceptable carrier, excipient, diluent or solvent.

7. The method as claimed in claims 1, 2, 3 or 4, wherein the composition comprising the betel leaf extract is administered orally or intramuscularly.

8. The method as claimed in claim 7, wherein when administered orally, the composition comprising betel leaf extract is in the form of a capsule, syrup, concentrate, powder or granules.

9. The method as claimed in claims 2 or 4, wherein the betel leaf extract and the additive are present in the composition at a ratio of between 10-1:1-10.

10. The method as claimed in claims 1, 2, 3 or 4, wherein the composition comprising the betel leaf extract is administered at a dosage level of between 5 to 10 mg/ml/kg of body weight at least once a day for one month.

11. The method as claimed in claims 2 or 4, wherein the additive is a selected from the group consisting of a protein, carbohydrate, sugar, talc, magnesium stearate, cellulose, calcium carbonate, and starch-gelatin paste.

12. A method for enhancing a cellular immune response mediated by $Th_1$ helper T-lymphocytes in a subject, said method comprising administering to a subject in need of such enhancing at least 5 to 10 mg/ml/kg of body weight of a composition comprising a betel leaf extract, wherein the betel leaf extract is obtained by aqueous extraction of betel leaves, wherein the composition is administered at least once a day for a period of at least one month, and wherein the composition is administered orally or intramuscularly, thereby enhancing a cellular immune response mediated by $Th_1$ helper T-lymphocytes.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: IFNgamma-sense

<400> SEQUENCE: 1
tctgcatcgt tttgggttct         20

<210> SEQ ID NO 2
<211> LENGTH: 20
<212> TYPE: DNA
<213> ORGANISM: Artificial Sequence -continued

```
<220> FEATURE:
<223> OTHER INFORMATION: IFNgamma-antisense

<400> SEQUENCE: 2
cagcttttcg aagtcatctc                                               20

<210> SEQ ID NO 3
<211> LENGTH: 20
<212> TYPE: DNA
<213> ORGANISM: Artificial Sequence
<220> FEATURE:
<223> OTHER INFORMATION: IL4-sense

<400> SEQUENCE: 3
cctctgttct tcctgctagc                                               20

<210> SEQ ID NO 4
<211> LENGTH: 20
<212> TYPE: DNA
<213> ORGANISM: Artificial Sequence
<220> FEATURE:
<223> OTHER INFORMATION: IL4-antisense

<400> SEQUENCE: 4
ccgtttcagg aatcggatca                                               20
```